United States Patent [19]
Blechman et al.

[11] Patent Number: 6,032,677
[45] Date of Patent: Mar. 7, 2000

[54] METHOD AND APPARATUS FOR STIMULATING THE HEALING OF MEDICAL IMPLANTS

[76] Inventors: Abraham M. Blechman, 93 Lester Dr., Tappan, N.Y. 10983; Jonathan J Kaufman, 112 Willow St., #1A, Brooklyn, N.Y. 11201

[21] Appl. No.: 09/116,913
[22] Filed: Jul. 17, 1998
[51] Int. Cl.[7] ................................................. A61B 19/00
[52] U.S. Cl. ................... 128/899; 600/9; 600/13; 600/14; 433/173; 433/189; 433/201.1; 433/215
[58] Field of Search ................ 128/899; 600/9, 600/13, 14; 433/173, 189, 201.1, 215

[56] References Cited

U.S. PATENT DOCUMENTS

| | | |
|---|---|---|
| 4,315,503 | 2/1982 | Ryaby et al. . |
| 4,530,360 | 7/1985 | Duarte . |
| 4,928,959 | 5/1990 | Bassett et al. . |
| 4,932,951 | 6/1990 | Liboff et al. . |
| 4,993,413 | 2/1991 | McLeod et al. . |
| 5,046,484 | 9/1991 | Bassett et al. . |
| 5,103,803 | 4/1992 | McLeod et al. . |
| 5,496,256 | 3/1996 | Bock et al. . |
| 5,520,612 | 5/1996 | Winder et al. . |
| 5,730,705 | 3/1998 | Talish et al. . |

OTHER PUBLICATIONS

Chavez H et al. "Assessment of oral implant mobility" The Journal of Prothetic Dentistry, vol. 70, No. 5 pp. 421–426, Nov. 1993.

Legerds RZ & Craig RG Strategies to affect bone remodeling: Osteointegration, Journal of Bone and Mineral Research, vol. 8, Supp. 2, pp. 5583–5596, 1993.

*Primary Examiner*—Max Hindenburg
*Assistant Examiner*—Brian Szmal
*Attorney, Agent, or Firm*—E. Lieberstein

[57] ABSTRACT

A technique to enhance the stability of dental and orthopedic implants (including artificial joints and fractures) by inducing implant micromotion via a permanent magnet coupled to the implant which is vibrated using a cyclic magnetic force to enhance growth and apposition of the surrounding bone. In the preferred embodiment the implant temporarily holds a rigidly fixed, permanent magnet that is oscillated by an externally applied, time varying moving magnetic field of controlled frequency and intensity. Movement of the internal magnet transmits movement to the implant and effects stimulation of the implant-bone interface.

28 Claims, 2 Drawing Sheets

METHOD AND APPARATUS FOR STIMULATING THE HEALING OF MEDICAL IMPLANTS

FIELD OF THE INVENTION

The present invention relates to medical implants and to a method to stimulate the healing of dental and orthopedic implants (including artificial joints and fractures) by causing controlled micro-loading of the implant and/or by generating a current flow through the implant so as to enhance growth and apposition of surrounding bone. Both micro-loading and/or generating current flow in the implant result from the application of an externally generated time-varying magnetic field with micro-loading of the implant caused by oscillating a permanent magnet secured, at least temporarily, to the implant.

BACKGROUND OF THE INVENTION

Several attempts to enhance bony ingrowth around an implant have been described in recent years. For example Rubin et. al. in a 1994 paper entitled "Promotion of Bony Ingrowth by Frequency-Specific, Low Amplitude Mechanical Strain" published in Clin. Ortho. Rel. Res. vol. 298, pp. 165–74 demonstrated that a 20 Hz, 150 microstrain mechanical loading to the bone surrounding a turkey ulnar implant (100 seconds a day) provided significant enhancement of fixation by increased bone growth into and apposition on the implant. Such mechanical loading has also been shown to be of benefit in the healing of bone fractures.

In another study on bone ingrowth by Tanzer et. al. in a 1996 paper entitled "Effect of Non-Invasive Low Intensity Ultrasound on Bone Growth in Porous Coated Implants" published in the J. Ortho Res. Vol. 14, No. 6, pp. 901–906, using an ultrasonic mechanical input demonstrated, that low intensity ultrasound (200 microsec of 1.5 MHZ sine at 10 kHz), externally applied for 20 minutes a day in a canine implant model, promoted bone ingrowth. This has also been shown clinically to promote fracture healing. Methods to increase bone incorporation (rate and amount) such as cellular grafts, electromagnetic stimulation, Ca—P coatings and growth factors have also been used clinically with various degrees of success.

Several patents also disclose methods and apparatus for bone growth stimulation. Ryaby et al. in U.S. Pat. No. 4,315,503 uses external inductively coupled electromagnetic fields to heal pseudoarthroses, and delayed and non-union bone fractures. Ryaby teaches the importance of using specific signal waveforms to ensure the effectiveness of the technique. The patent is based upon the application of asymmetric periodic pulsed waveforms, whose choice is motivated by the endogenous electrical signals in bone induced by external strains. Another patent by Liboff et al., U.S. Pat. No. 4,932,951 teaches apparatus and method to heal bone fractures using inductively coupled low frequency sinusoidal electromagnetic signals. The specific frequency is based on a "cyclotron-resonance" condition, which is supposed to affect the trajectory of specific cations, for example, calcium. It is hypothesized that modulation of cation motion can stimulate the formation of bone. In a related patent U.S. Pat. No. 4,993,413 a method and apparatus is taught to prevent osteoporosis and to enhance new bone formation using a low frequency inductively coupled sinusoidal signal in the frequency range 15 and 75 Hertz.

A method and device are also described in U.S. Pat. Nos. 4,928,959 and 5,046,484 for increasing the amount, strength and proper anatomical distribution of bone in a patient suffering from a bone disorder based upon the use of mechanical stimuli to stimulate bone growth. These patents involve the use of an impulsive or impact force in which the subject experiences a force similar to that obtained in normal walking. In yet another U.S. Pat. No. 5,103,806 to McLeod et al., a method is described for preventing osteopenia by subjecting the subject to a sinusoidal mechanical stimulation signal in the frequency range of 10 and 100 Hertz. The patent points out the advantage of using "a relatively high frequency" in that it subjects the patient to less physical trauma compared with the impact approach taught by Bassett et al.

An excellent review of methods proposed to stimulate bone ingrowth around artificial implants (known as "osteointegration") has been published in 1993 in the Journal of Bone and Mineral Research in vol. 8, Supplement 2 entitled "Strategies to Affect Bone Remodeling: Osteointegration" by Racquel Z. Legeros and Ronald G. Craig. These methods include biomechanical, biological and biomaterial factors which affect integration of the implant into the endogenous bone.

In all of the above prior art, there is either a lack of effectiveness to enhance osteointegration and implant stability and/or a shortcoming with respect to the means available to apply biomechanical stimuli appropriate to the implant bone interface. The present invention addresses both of these shortcomings.

An interesting paper authored by Chavez et al. entitled "Assessment of oral implant mobility" published in the Journal of Prosthetic Dentistry, vol. 70, number 5, 1993 challenges the commonly accepted notion that dental implants must be totally immobile to be successful. Using a very sensitive Periotest device, the authors demonstrated that clinically successful endosseous implants could be displaced from 0.038 mm to 0.113 mm with a mean of 0.66 mm (66 $\mu$m). Micromotion in accordance with the present invention is based upon amplitude displacement between 0.1 $\mu$m, to 20 $\mu$m.

It is also noteworthy that three papers (Holcolm et al. "Biomagnetics in the treatment of human pain: past, present, future in Environ Med, 1991a; 8:24–30, McLean et al. "Blockade of sensory neuron action potentials by a static magnetic field in the 10 mT range" in Bioelectromagnetics 1995; 16:20–32, and Cavopol et al. "Measurement and analysis of static magnetic fields that block action potentials in cultured neurons" in Bioelectromagnetics 1995; 16:197–206) demonstrate that static magnetic fields are capable of reducing pain. Additional corroborating evidence already exists in the clinical orthodontic literature.

SUMMARY OF THE INVENTION

In accordance with a preferred embodiment of the present invention a permanent magnet is secured, at least temporarily, to the implant during which time a time varying magnetic field of controlled frequency and intensity is applied to the permanent magnet to cause the permanent magnet to oscillate. The force exerted on this internal magnet by an externally generated time-varying magnetic field is transmitted to the implant and generates implant micromotion. Since conventional implants are composed of metal such as titanium which is highly conductive, the application of a time varying magnetic field at an appropriate frequency and intensity in close proximity to the implant will induce current flow through the implant. This current flow may be used in accordance with the present invention independent of or in concert with microloading of the implant. Although induced current flow may be used in concert with any known technique which will cause implant microloading as discussed heretofore in the background of the invention it is preferred that implant micromotion be generated by oscillation of an internal magnet secured to the implant. A permanent magnet secured to the implant may also be used in accordance with the present invention to generate a static magnetic field for reducing pain.

Inducing current flow in an implant composed of a conductive metal by application of an external time varying magnetic field is conceptually different from the past practice of electromagnetic stimulation of a fracture site where no implant device was used. In addition to titanium commonly used for dental implants, other metals such as chrome-cobalt and various other metals or alloys have been contemplated for use as implants in orthopedic applications. All of these are also good electrical conductors such that upon application of an externally applied electromagnetic field of appropriate intensity and frequency, current will be induced to flow in the embedded implant. It should be understood that live bone is porous and that the fluid which permeates live bone is known to be electrolytic. Accordingly, the current induced in the implant completes an electrical circuit through the fluid in bone and the implant. It should be further understood that the electrical conductivity of the implant is much higher than that of surrounding tissue. Therefore the generation of high in-situ current is an advantage not achievable heretofore. Additionally, current flow is also induced by the stimulation of the external magnetic field on electrically charged tissue electrolytes within the body which are moving through the magnetic field.

It was further discovered in accordance with the present invention that the osteogenic rate of bone growth surrounding dental and orthopedic implants can be accelerated solely by inducing current flow through the implant or preferably by causing implant micromotion under controlled conditions in which a permanent magnet is at least temporarily connected to the implant and vibrated by application of an externally generated time varying magnetic field which may, under appropriate conditions, also induce current in the implant. For example, frequency control in the external magnetic device generates higher frequencies which can increase current flow in the implant (up to $100\mu$ amperes) or lower frequencies which can enhance micromotion.

In accordance with the present invention the externally induced time varying magnetic field can be generated by any known method such as by moving another permanent magnet or by moving a shield surrounding or partially surrounding a permanent magnet. The oscillating force on the implanted magnet transmits a force to the implant resulting in oscillating microloading of the implant and an induced oscillatory micromotion at the implant-bone interface. As explained earlier microloading of the implant is known to stimulate cellular activity conducive to bone ingrowth.

In accordance with one embodiment of the present invention bone growth is stimulated at the interface between a medical implant of an electrically conductive composition and surrounding bone into which the medical implant has been surgically inserted by a method comprising the steps of generating a magnetic field external to the embedded implant in relative close proximity thereto with the magnetic field being of sufficient field strength and of a given frequency to induce current flow through the implant, maintaining the magnetic field in such close proximity to the implant for a fixed time period of at least 1 minute and periodically repeating the procedure.

Another embodiment of the present invention for stimulating bone growth at the interface between a medical implant and surrounding bone into which the medical implant has been surgically inserted comprises the steps of: attaching a permanent magnet to the medical implant and oscillating the magnet by means of a time varying magnetic field having sufficient field strength to cause the implant to vibrate within a preferred amplitude range of 0.01 $\mu$m to 20 $\mu$m.

The medical implant of the present invention comprises, in combination, a metal body having a cavity, a member which is removably inserted into said cavity, a permanent magnet adapted to be affixed to said member and external means for microloading the implant when surgically inserted into bone by application of a time varying magnetic field in close proximity to the permanent magnet to cause accelerated osteogenic bone growth at the interface between the implant and the surrounding bone.

DETAILED DESCRIPTION OF THE PREFERRED EMBODIMENTS

Figure 1A:
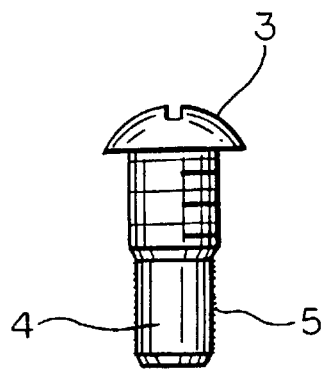
FIG. 1(a) is a cross sectional view of a healing screw cap adapted to be removably inserted into the dental implant of FIG. 1(b) with the healing screw cap having a permanent magnet secured thereto.
Figure 1B:
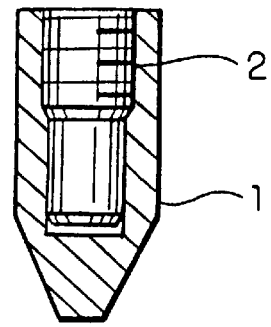
FIG. 1(b) is a diagrammatic view in cross section of a typical dental implant adapted to be embedded in the jawbone of a patient.

To provide adequate structural support for attachment of a dental restoration to a dental implant it is essential that cellular bone growth or bone ingrowth occur at the bone-implant interface to effect implant consolidation. This requires a substantial time period following surgery for implant insertion of typically 6–9 months during which time the implant remains buried and useless. FIG. 1(b) illustrates a conventional dental implant 1 to be surgically inserted into the jawbone of a dental patient. The implant 1 is composed primarily of titanium and has dimensions of, for example, 7–13 mm length×3.5 mm diameter. A temporary screw cap 3 as shown in FIG. 1(a) having, for example, screw thread outer dimensions of 1.1 mm O.D.×2.5 mm long, is affixed within a cavity 2 formed in the body of the titanium implant 1 to keep the cavity 2 free of tissue during the time period the cap 3 is used during initial healing. The cap 3 is preferably a screw-on cap and the cavity 2 is preferably a threaded cavity into which the cap 3 is threadably engaged.

Figures 1C, 1D:
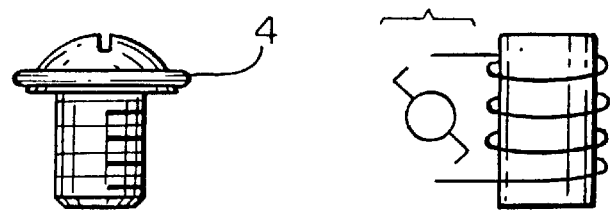
FIG. 1(c) is a variation of a healing cap and permanent magnet arrangement in accordance with the present invention.
FIG. 1(d) shows an electromagnetic oscillator for vibrating the permanent magnet in FIG. 1(a) or FIG. 1(c)
Figure 3:
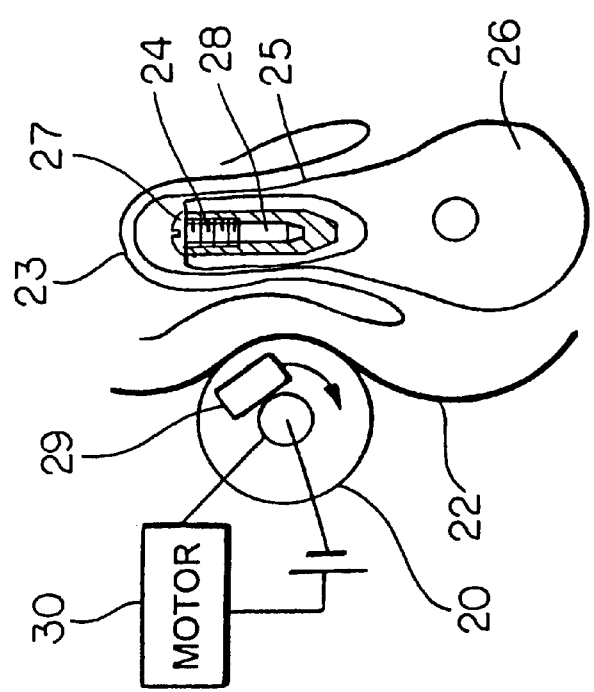
FIG. 3 shows a cross-sectional frontal view of an external magnet located adjacent to an embedded dental implant with an internal magnet attached to a healing screw cap in a jawbone and with the external magnet attached to a motor for rotation about a given axis to produce a time varying magnetic field in accordance with the present invention.

In accordance with the present invention a permanent magnet 4 is connected at the one end of the cap 3 that resides internally within the implant in FIG. 1b during the period of normal healing. The permanent magnet 4 is composed of SmCo or NdFeB or any ferromagnetic material and is coated with a biocompatible adhesive hermetic sealant 5 attaching the magnet 4 to the screw cap 3 before insertion of the cap 3 into the cavity 2. The preferred arrangement is to rigidly connect the magnet 4 to the underside of the cap 3 using e.g. a medical grade adhesive epoxy or a conventional parylene C polymer composition which both coats and affixes the magnet 4 to the cap 3 so that insertion and removal of the cap 3 also inserts and removes the magnet 4 from the cavity 2. Alternatively the permanent magnet 4 (which is larger) may be connected to the top or head of the screw-on healing cap 3 as shown in FIG. 1(c) preferably with the magnet 4 having a torroid or donut shape so that access to the screw-on cap 3 is available through the hole in the magnet 4. A controlled oscillating magnetic field may be generated external of the implant in any conventional manner. In FIG. 3 a permanent magnet 29 is rotated by a small electrically powered motor 30 protected in a housing 20. Alternatively, the housing 20 may represent a movable shield surrounding the permanent magnet 29 in which the shield is reciprocated by means not shown in a traverse direction relative to the magnet to apply a time varying field. The shield may alternatively have a longitudinal slot (not shown) in which instance it may be rotated about the magnet to generate the time varying magnetic field. Independent of how the external magnetic field is generated its source should be placed in close proximity to the implant 1 and the permanent magnet 4. It should be understood that current can be induced in the implant under appropriate conditions of higher frequency and intensity which may not necessarily be at the optimum conditions for causing micromotion which requires lower frequency. It is possible to both cause micromotion under optimum conditions and to also apply a time varying field under varying frequency conditions which will induce current flow where the combined effect is preferred. It is also possible to cause an induced current to flow through an implant without any induced micromotion, for example by not using an internal magnet.

In the embodiment of FIG. 3 the rotating magnet 29 is held with pressure against the external surface of the cheek 22 or intraorally against the gingiva 23 or in any desired position near the implant 24 embedded in the alveolar bone 25 of the mandible 26. The healing cap 27 is placed inferior to the mucoperiosteal flap which is the superior section of the gingiva 23 covering the healing screw cap 27. The internal magnet 28 is affixed to the inferior end of the healing cap 27 which is threadably secured within the implant 24.

External stimulation begins several days following surgical insertion and is to be applied for at least 1 minute, preferably at least 5 minutes although optimally for 10 to 30 minutes at periodic intervals such as daily and for a period of 3 to six weeks or until an x-ray and/or a torque testing device demonstrates implant consolidation. After healing, the temporary cap 3 with the attached magnet 4 is removed to permit a permanent restorative dental device to be attached to the implant by using, for example, a threaded post (not shown). Multiple implants may be implanted and stimulated at the same time. The external magnet may be located inside the mouth, preferably temporarily attached to the teeth over the implant site to avoid holding the external magnet by hand. This temporary attachment to the teeth in the opposing jaw may also occur so that normal jaw movement will initiate the time varying magnetic stimulation to the magnet inside the implant, therby stimulating micromotion of this internal magnet and implant.

The strength of the magnetic field utilized in the present invention depends on the specific amount of vibration or micromotion which is desired to be induced. In the preferred embodiment of FIG. 3 the internal permanent magnet 28 affixed to the inferior end of the threaded healing screw 27 placed in the implant 24 embedded in the jawbone of the patient is composed of samarium-cobalt e.g. having a 28MGOe energy product and the external rotating magnet 29 is composed of neodymium-iron-boron with a 44 MGOe energy product although this invention is not to be construed as limited to such magnets or magnetic field strengths.

Figure 2:
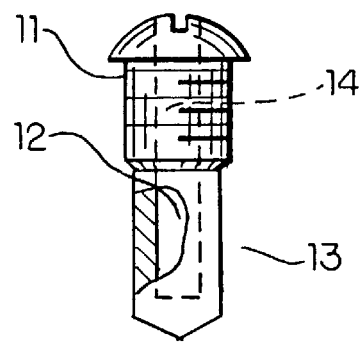
FIG. 2 shows a typical orthopedic cannulated screw in an arrangement with a magnet located within the cannulated portion.

A medical cannulated screw such as used in an orthopedic implant, as shown in FIG. 2 may be inserted into an artificial joint implant, orthopedic implant, fracture plate, or used by itself. The medical implant of FIG. 2 comprises a threaded orthopedic cannulated screw 11 of varying lengths from 10 mm to 75 mm and widths of from 2.7 mm to 6.5 mm. In accordance with the present invention a permanent magnet 12 is placed into the cannulated portion 14 of the screw 11 and is coated with medical epoxy longitudinally 13 and at the closed end. A permanent magnet 12 which may be of 1.2 mm to 2 mm in width corresponding to the internal width of the cannulated portion of the screw 11. The length of the permanent magnet 12 will depend on the length of the screw. The magnet can be made of materials such as SmCo, NdFeB or any ferromagnetic material. The screw can be inserted in or near a fracture or into a threaded cavity in a joint implant. After implant healing the screw may be removed or left in place. A controlled oscillating magnetic field is applied by an external electromagnet (or other means such as described above in connection with the dental implant) for causing the implant to vibrate with micromotion. An externally applied magnetic field will cause the coupled magnet/implant complex to be oscillated at a controlled frequency and amplitude. Stimulation may be applied for 1 to 30 minutes a day for a period of 6 weeks or until an x-ray demonstrates fracture healing or implant consolidation. After implantation and healing of the surrounding bone, the screw 11 and permanent magnet may be removed or left in place.

Figure 4:
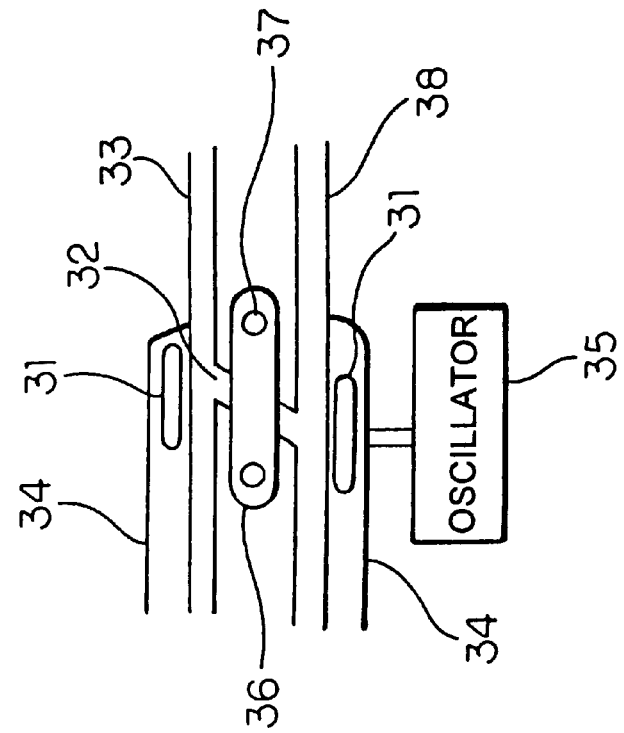
FIG. 4 illustrates an arrangement of permanent magnets for medical application to induce bone micromotion of a fracture site in accordance with the present invention by an external time varying magnetic field when metal internal fixation is necessary.

At least one oscillating magnet but preferably a pair of magnets, 3, 31, may be arranged as shown in FIG. 4 for a medical application of e.g. to treat bone fractures 32 (e.g. long bone fractures) with the application of a metal plate for internal fixation. The magnet or magnet(s) should be placed directly over the underlying bone fracture on the skin surface 33 and embedded in a fixation device such as a plastic cast 34. When a pair of oscillating magnets 31, 31 are used, the magnets should be placed, for example, on the dorsum and volar surfaces of the wrist in an attractive aiding mode relative to one another. The magnets may be circular or square in shape with the flat or longer surface areas as the pole faces. An external magnet field via oscillator 35 is then generated and then applied to the magnets 31, 31 to cause them to vibrate so as to induce micromotion in the bone. When internal rods are used for tibial internal fixation for example, the rod may be hollow and contain magnets. It should be understood that the invention includes use of one or more permanent magnets to therapeutically treat bone fractures whether or not the fracture is fixed i.e., to treat bone fractures with or without metal fixation. In this case, the permanent magnet or magnets are moved (i.e., oscillated) or shielded in a time dependent fashion to generate an external time-varying magnetic field. It should be further understood that such therapeutic treatment can be applied to all biological tissues not just bone. Finally, as already disclosed the method can rely on only a permanent magnet although more than one can be used as well.

When metal plates 36 are required for fracture internal fixation, the cannulate screws 37 (similar to 11 in FIG. 2) used to hold the plates in position on both fracture fragments, may contain magnets and may be stimulated into micromotion with external time-varying magnetic fields, as previously described.

It should be understood that the magnetic field strengths necessary to achieve a particular degree of micromotion will depend on a variety of factors specific to a particular application. For example, in the case of dental implants, the relatively small size of the internal magnet requires a relatively strong external magnetic field. In addition, the degree of micromotion can be computed quantitatively. The 1993 publication by Hugo Chavez and others entitled "Assessment of oral implant mobility" in the Journal of Prosthetic Dentistry, Volume 70, Number 5, pp. 421–426, for example, provides a quantitative characterization of the amount of force that can move a typical successful dental implant a specific number of millimeters or microns as noted previously. Since most of the implant literature suggests that successful implants are immobile and any mobility indicates implant failure, it might appear that micromotion is not possible with successful implants. However, this article clearly demonstrates and documents using a sophisticated Periotest instrument that a range of motion from 0.038 mm (38 µm) to 0.113 mm (113 µm) with a mean of 0.66 mm (66 µm) exist for successful implants. Therefore micromotion in accordance with the present invention of between 0.01 µm to 20 µm is clearly realistic.

It is understood by those skilled in the art how to choose appropriate magnetic field exposures for a specific amount of induced micromotion. It should also be appreciated that the induced micromotion may achieve its intended benefits by virtue of the fact that the applied micromotion is of a time dependent nature, and that it may include the use of relatively high frequencies associated with the mechanical input. Thus, although micromotion as small as 0.01 microns may be generated, the time-dependent nature of the implant's displacement can nevertheless be effective in stimulating bone growth and accelerating stability of the implant. The preferred amplitude range for vibration of an implant is between 0.01 µm and 20 µm. The permanent magnet 4 may be oscillated within a preferred frequency range of between 0.1–10,000 Hz although frequencies can be applied up to 1 Gigahertz.

It should be further understood that there are a variety of methods which may be used to generate the time varying external magnetic field. For example, instead of a permanent magnet rotating on an axis, one can also use a fixed permanent magnet alternately exposed and covered by a mu-metal shield. This produces an external time-varying magnetic field which generates a mechanical micromotion of the implant through the forces induced on the implant permanent magnet. As a further alternative embodiment of the present invention, the external magnetic field may be produced using an inductively coupled field, generated by currents flowing through an external electrical coil (e.g. an "electromagnet"). The latter embodiment has the advantage of no moving (mechanical) parts. This can be advantageous in certain instances such as for achieving a higher range of vibration (i.e., micromotion) frequencies. Thus it should be understood that there are a number of ways in which the external magnetic field can be generated. It should also be pointed out that the use of the invention may rely on the external magnet being placed at various locations on the patient. In the presently preferred embodiment as exemplified in FIG. 3, the patient holds a small fixture containing a rotating permanent magnet tightly against his or her cheek, to reduce the intermagnet separation distance, in order to induce the desired micromotion of the implant. Alternatively, the fixture may be placed directly into the mouth closer to the implant to further decrease the separation distance. In a similar but alternative embodiment, the external magnet is affixed within the mouth on the jaw opposite to the jaw in which the implant or implants are placed. In this case, the changing positions of the upper and lower jaws relative to one another (through the course of normal activities) induces a varying magnetic field exposure on the implant and thereby associated therapeutic and beneficial effects. The size of the external magnet, or more generally the magnitude of the external field, will depend on the distance between the source of the external field and the internal field, i.e. the air gap, separating the external magnet from the internal magnet. Obviously, different external field strengths may be required to account for different thickness variations in soft tissue separating the source of the external field from the internal magnet e.g. for use by both obese and slim patients.

Yet another embodiment of the invention is the use of an internal magnet secured inside or outside to an implant without the application of an external magnetic field. In this case the static or DC magnetic field by itself will cause a beneficial therapeutic effect in relieving pain and enhancing osteogenesis.

Finally, it should be pointed out that the present invention includes a wide range of possible temporal characteristics associated with the induced micromotion or vibration. In the practice of the preferred embodiment of the present invention micromotion has a sinusoidal motion although other waveforms may equally be used.

What we claim is:

1. A method for enhancing the stability of a medical implant surgically inserted into bone by stimulating bone growth at the interface between the implant and surrounding bone comprising the steps of: attaching a permanent magnet to the implant and exposing the magnet to an externally applied time varying magnetic field having sufficient field strength to cause the implant to vibrate with micromotion.

2. A method as defined in claim 1 wherein said magnet is oscillated at a frequency in a range between 0.1–10,000 Hz.

3. A method as defined in claim 2 wherein the magnitude of the amplitude of said vibration is maintained below 20 µm.

4. A method as defined in claim 3 wherein the amplitude magnitude of said vibration is maintained between 0.01 and 10 µm.

5. A method as defined in claim 3 wherein said permanent magnet is composed of a material selected from the group consisting of NdFeB, ferrite, SmCo and Alinico and any other ferromagnetic material.

6. A method as defined in claim 5 wherein said permanent magnet is connected to a member removably affixed to said implant.

7. A method as defined in claim 6 wherein said member is a screw removably inserted into a cavity formed in said implant.

8. A method as defined in claim 7 wherein said permanent magnet is mounted to said screw at the proximal end thereof so as to be secured within the interior of the implant.

9. A method as defined in claim 6 wherein said implant is a dental implant.

10. A method as defined in claim 6 wherein said implant is a medical orthopedic joint implant.

11. A method as defined in claim 10 wherein said implant includes a metal plate with corrugated screws and a permanent magnet for the treatment of fractured bones.

12. A method as defined in claim 1 further comprising the step of inducing a current flow in the implant.

13. A method for enhancing the stability of a medical implant surgically inserted into bone by stimulating bone growth at the interface between the embedded implant and surrounding bone comprising the steps of: generating a magnetic field external to the embedded implant in relative close proximity thereto with the magnetic field being of sufficient field strength and of a given frequency to induce current flow through the implant, maintaining the magnetic field in such close proximity to the implant for a fixed time period of at least 1 minute and periodically repeating the procedure.

14. A method as defined in claim 13 further comprising the step of inducing micromotion in said implant.

15. A method for enhancing the therapeutic benefit of a medical implant surgically inserted into a human comprising the step of securing a permanent magnet to the implant.

16. Medical implant apparatus comprising in combination, a metal body having a cavity, a removable screw for engaging said cavity in said metal body and a permanent magnet adapted to be affixed to said removable screw.

17. Medical implant apparatus according to claim 16 further comprising means for non-invasively inducing time varying micromotion of said permanent magnet following the surgical insertion of said implant in bone for accelerating osteogenic bone growth at the bone-implant interface.

18. Medical implant apparatus as defined in claim 17 wherein said means for non-invasively inducing time varying micromotion of said permanent magnet comprises at least one electric coil.

19. Medical implant apparatus as defined in claim 17 wherein said means for non-invasively inducing time varying micromotion of said permanent magnet comprises another permanent magnet, means for rotating said other permanent magnet and a housing for said other permanent magnet.

20. Medical implant apparatus as defined in claim 17 wherein said means for non-invasively inducing time varying micromotion of said permanent magnet comprises another permanent magnet, means for shielding said other permanent magnet and means for moving said shielding means to generate said time varying magnetic field.

21. Medical implant apparatus comprising in combination, a metal body of a conductive material adapted to be surgically inserted into bone and means for inducing current flow through said metal body after it is surgically implanted.

22. Medical implant apparatus as defined in claim 21 wherein said means for inducing current flow is a time varying magnetic field generated from a permanent magnet.

23. Medical implant apparatus as defined in claim 22 further comprising means for moving said permanent magnet to generate said time varying magnetic field.

24. Medical implant apparatus as defined in claim 22 further comprising means for shielding said permanent magnet and means for moving the shielding means to generate said time varying magnetic field.

25. Medical implant apparatus as defined in claim 22 further comprising a static magnetic field.

26. Apparatus for therapeutically treating tissue in a human body comprising a permanent magnet to generate a time varying magnetic field with the permanent magnet being located in close proximity to the tissue to be treated.

27. Apparatus as defined in claim 26 further comprising means for moving said permanent magnet to generate said time varying magnetic field.

28. Apparatus as defined in claim 26 further comprising means for shielding said permanent magnet and for moving said shielding means to generate said time varying magnetic field.

* * * * *